United States Patent [19]

Chester et al.

[11] 4,283,584

[45] Aug. 11, 1981

[54] MANUFACTURE OF AROMATIC COMPOUNDS

[75] Inventors: Arthur W. Chester; Yung F. Chu, both of Cherry Hill, N.J.

[73] Assignee: Mobil Oil Corporation, New York, N.Y.

[21] Appl. No.: 140,346

[22] Filed: Apr. 14, 1980

[51] Int. Cl.³ .......................... C07C 5/22; C07C 4/12
[52] U.S. Cl. ..................................... 585/481; 208/66; 585/489
[58] Field of Search ................... 585/481, 488; 208/66

[56] References Cited
U.S. PATENT DOCUMENTS

| | | | |
|---|---|---|---|
| 3,856,871 | 12/1974 | Heag et al. | 585/481 |
| 4,100,214 | 7/1978 | Dwyer | 585/481 |
| 4,101,595 | 7/1978 | Chen et al. | 585/481 |
| 4,101,597 | 7/1978 | Breckenridge | 585/481 |
| 4,218,573 | 8/1980 | Tabak et al. | 585/489 |
| 4,236,996 | 12/1980 | Tabak et al. | 585/481 |

*Primary Examiner*—Curtis R. Davis
*Attorney, Agent, or Firm*—C. A. Huggett; M. G. Gilman; C. J. Speciale

[57] ABSTRACT

Isomerization of xylenes admixed with other alkyl aromatics of at least eight carbon atoms and with normal or slightly branched paraffins is conducted at 800°–1000° F. with a zeolite like zeolite ZSM-5 of reduced acid activity.

44 Claims, 1 Drawing Figure

MANUFACTURE OF AROMATIC COMPOUNDS

FIELD OF THE INVENTION

The invention is concerned with manufacture of aromatic compounds having six ($C_6Ar$) to eight ($C_8Ar$) carbon atoms, namely benzene, toluene and xylene (BTX). At the present time, the most valuable of these is p-xylene, which may be separated for use in synthesis of polyesters from mixed xylenes by fractional crystallization. Also highly valued is benzene for use as chemical raw material. Toluene is also valuable for varied uses as solvent, in chemical manufacture and as a high octane gasoline component.

According to the present invention, available raw materials such as reformed petroleum naphthas (reformate) are processed to yield p-xylene as the principal product and to produce toluene and benzene as substantially the sole aromatic by-products.

BACKGROUND OF THE INVENTION

Typically, p-xylene is derived from mixtures of $C_8$ aromatics separated from such raw materials as petroleum naphthas, particularly reformates, usually by selective solvent extraction. The $C_8$ aromatics in such mixtures and their properties are:

|              | Freezing Point °F. | Boiling Point °F. | Density Lbs./U.S. Gal. |
|--------------|--------------------|-------------------|------------------------|
| Ethylbenzene | −139.0             | 277.0             | 7.26                   |
| P-xylene     | 55.9               | 281.0             | 7.21                   |
| M-xylene     | −54.2              | 282.4             | 7.23                   |
| O-xylene     | −13.3              | 292.0             | 7.37                   |

Principal sources are catalytically reformed naphthas and pyrolysis distillates. The $C_8$ aromatic fractions from these sources vary quite widely in composition but will usually be in the range 10 to 32 wt.% ethylbenzene with the balance, xylenes, being divided approximately 50 wt.% meta, and 25 wt.% each of para and ortho.

Individual isomer products may be separated from the naturally occurring mixtures by appropriate physical methods. Ethylbenzene may be separated by fractional distillation although this is a costly operation. Ortho xylene may be separated by fractional distillation and is so produced commercially. Para xylene is separated from the mixed isomers by fractional crystallization.

As commercial use of para and ortho xylene has increased there has been interest in isomerizing the other $C_8$ aromatics toward an equilibrium mix and thus increasing yields of the desired xylenes, as by OCTAFINING.

In a typical plant for utilization of Octafining, a mixture of $C_8$ aromatics is introduced to an ethylbenzene tower wherein the stream is stripped of a portion of its ethylbenzene content, to an extent consistent with retaining all the xylenes in the feed stream without unduly expensive "superfractionation". Ethylbenzene is taken overhead while a bottom stream, consisting principally of xylenes, together with a significant amount of ethylbenzene, passes to a xylene splitter column. The bottoms from the xylene splitter constituted by o-xylene and $C_9$ aromatics passes to the o-xylene tower from which o-xylene is taken overhead and heavy ends are removed. The overhead from the xylene splitter column is transferred to conventional crystallization separation. The crystallizer operates in the manner described in Machell et al., U.S. Pat. No. 3,662,013 dated May 9, 1972.

Because its melting point is much higher than that of the other $C_8$ aromatics, p-xylene is readily separated in the crystallizer after refrigeration of the stream and a xylene mixture lean in p-xylene is transferred to an isomerization unit. The isomerization charge passes through a heater, is admixed with hydrogen and the mixture is introduced to the isomerizer.

Isomerized product from the isomerizer is cooled and passed to a high pressure separator from which separated hydrogen can be recycled in the process. The liquid product of the isomerization passes to a stripper from which light ends are passed overhead. The remaining liquid product constituted by $C_8+$ hydrocarbons is recycled in the system to the inlet of the xylene splitter.

It will be seen that the system is adapted to produce quantities of p-xylene from a mixed $C_8$ aromatic feed containing all of the xylene isomers plus ethylbenzene. The key to efficient operation for that purpose is in the isomerizer which takes crystallizer effluent lean in p-xylene and converts the other xylene isomers in part to p-xylene for further recovery at the crystallizer.

Among the xylene isomerization processes available in the art, Octafining was originally unique in its ability to convert ethylbenzene. Other xylene isomerization processes have required extremely expensive fractionation to separate that component of $C_8$ aromatic fractions. As will be seen from the table of properties above, the boiling point of ethylbenzene is very close to those of p and m-xylene. Complete removal of ethylbenzene from the charge is impractical. The usual expedient for coping with the problem was an ethylbenzene separation column in the isomerizer-separator loop when using catalyst other than those characteristic of Octafining. It will be seen that Octafining does not need this expensive auxiliary to prevent build up of ethylbenzene in the loop. This advantageous feature is possible because the Octafining catalyst converts ethylbenzene.

In Octafining, ethylbenzene reacts through ethyl cyclohexane to dimethyl cyclohexanes which in turn equilibrate to xylenes. Competing reactions are disproportionation of ethylbenzene to benzene and diethylbenzene, hydrocracking of ethylbenzene to ethane and benzene and hydrocracking of alkyl cyclohexanes.

A significant improvement arose with the introduction of catalysts such as zeolite ZSM-5 combined with a metal such as platinum as described in Morrison U.S. Pat. No. 3,856,872. At temperatures around 700°–800° F., ethylbenzene is converted by disproportionation over this catalyst to benzene and diethylbenzene. At higher temperatures and using a zeolite ZSM-5 catalyst of reduced activity, ethylbenzene and other single ring aromatics are converted by splitting off side chains of two or more carbon atoms as described in copending application Ser. No. 914,645, filed June 12, 1978, now U.S. Pat. No. 4,188,282.

These developments permit upgrading of Octafining reactors by substitution of the improved (ZSM-5) catalyst.

In the known processes for accepting ethylbenzene to the loop, conversion of that compound is constrained by the need to hold conversion of xylenes to other compounds to an acceptable level. Thus, although the Morrison technique provides significant advantages over Octafining in this respect, operating conditions are still selected to balance the advantages of ethylbenzene conversion against the disadvantages of xylene loss by disproportionation and the like.

A further advance in the art is described in copending applications of Morrison and Tabak directed to various techniques for reducing acid activity of zeolite ZSM-5 catalyst and use of such low activity catalysts for xylene isomerization concurrently with ethylbenzene conversion at temperatures upwards of 800° F. One such copending application is Ser. No. 912,681, filed June 5, 1978, now U.S. Pat. No. 4,163,028, which discloses xylene isomerization and ethylbenzene conversion at high temperature with ZSM-5 of very high silica/alumina ratio whereby the acid activity is reduced.

The inventions of those copending applications are predicated on discovery of combinations of catalyst and operating conditions which decouples ethylbenzene conversion from xylene loss in a xylene isomerization reaction, thus permitting feed of $C_8$ fractions which contain ethylbenzene without sacrifice of xylenes to conditions which will promote adequate conversion of ethylbenzene. These results are obtained by use of a catalyst characterized by zeolite ZSM-5 substantially reduced in activity as by dilution, steaming, very high silica/alumina ratio, base exchange with alkali metal, coking or the like. At the high temperatures of 800°–1000° F., the zeolite of reduced activity exhibits effective power for isomerization of xylene and for splitting off alkyl side chains of two or more carbon atoms from single ring aromatics at long on-stream periods. The disproportionation activity of the zeolite is severely depressed by the reduced acid activity, resulting in low losses of xylene by that mechanism. That lack of disproportionation activity impairs the capacity of the catalyst to handle trialkyl aromatics of nine of more carbon atoms, e.g. trimethylbenzene, as practiced in some processes. It thus becomes necessary to remove from the recycle stream those components having more than eight carbon atoms to avoid excessive build-up in the system of $C_9$ and higher. The catalyst also has the capacity to crack paraffins in the charge to lower boiling compounds readily removable from recycle streams by fractionators normally present in the p-xylene recovery/isomerizer loop.

By reason of this combination of activities, the catalyst may be used in a system charging reformate without removal of paraffin hydrocarbons as described in application Ser. No. 945,279, filed Sept. 25, 1978, now U.S. Pat. No. 4,211,886.

SUMMARY OF THE INVENTION

It has now been found that advantages in high temperature xylene isomerization over low acidity zeolites similar to ZSM-5 plus a metal result from inclusion in the charge to the isomerizer of normal and/or slightly branched paraffins in amounts greater than that found in reformate.

BRIEF DESCRIPTION OF THE DRAWING

The single FIGURE of the drawing is a diagrammatic representation of the principal elements in a conventional plant for preparation of p-xylene by the low pressure isomerization technique. Processing equipment which may be retired from service or reduced in service load for operation according to the invention are indicated by enclosure in broken lines, marked "optional".

DESCRIPTION OF SPECIFIC EMBODIMENTS

The essence of the invention is the versatile and efficient isomerization reactor which can also serve for selective dealkylation of single ring aromatic compounds to remove alkyl side chains of two or more carbon atoms. That reactor is characterized by a zeolite catalyst having a silica/alumina ratio of at least 12, a constraint index as hereinafter defined between about 1 and 12 and a reduced acid activity also defined below. The zeolite catalyst is combined with a hydrogenation metal from Group VIII of the Periodic Table, e.g. cobalt, nickel, platinum, palladium, etc. The reactor is maintained at a temperature of 800° to 1000° F. and a pressure above about 100 pounds per square inch, guage (psig). Very high pressures require excessively expensive facilities and are generally avoided for economic reasons although it does not appear that such pressures have any adverse effect on the reaction. For the reason stated, pressures employed will generally be not greater than 2000 psig.

Figure 1:
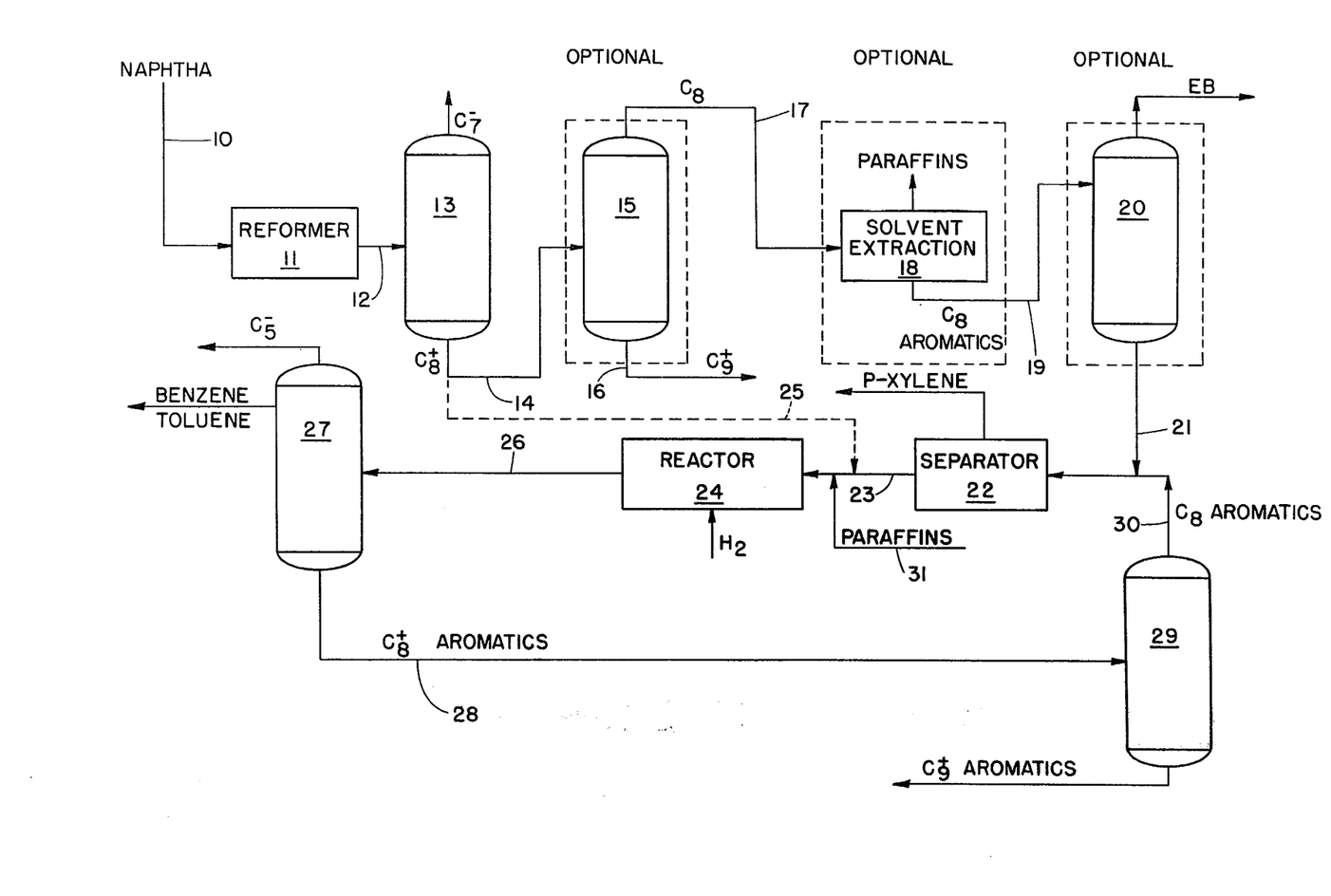

As shown in the annexed drawing, the reactor of this invention may be incorporated in a reaction train through which a petroleum naphtha is processed for manufacture of p-xylene. Alternatively, the process of the invention may be used in a facility charging purchased $C_8$ aromatics or mixed xylenes. In the embodiment here illustrated, a light petroleum naphtha supplied by line 10 is charged to a reformer 11 operated to convert naphthenes to aromatics by dehydrogenation under hydrogen pressure over a catalyst of platinum supported on alumina.

The aromatic rich reformate product of reformer 11 is transferred by line 12 to fractionator 13 operated to take compounds of seven or less carbon atoms overhead, leaving a bottom fraction of eight or more carbon atoms which may be transferred by line 14 to fractionator 15. Alternatively, the bottoms of column 13 may pass directly to the solvent extraction stage or to the reactor, both presently to be described. Assuming utilization of fractionator 15, a bottoms fraction at line 16 is constituted by hydrocarbons of nine or more carbon atoms, rich in aromatics. The fraction in line 16 may be used as a component of high octane motor fuel or processed to convert its aromatic content to a mixture of benzene, toluene and xylenes (BTX).

The eight carbon atoms overhead of fractionator 15 is shown transferred by line 17 to a solvent extraction stage 18 wherein paraffins are separated by use of a suitable solvent in known manner. Alternatively, the $C_8$ overhead of fractionator 15 may be passed directly to the reactor. The $C_8$ aromatic fraction prepared by the solvent extraction stage 18 is preferably transferred by line 19 to a stripper 20 for removal of ethylbenzene. The degree of ethylbenzene removal, if practiced, may be accommodated to the desires of the operator, since the reactor of this invention can tolerate considerable amounts of ethylbenzene, which is thereby converted to benzene.

In any event, fresh feed to the isomerizer loop is constituted by bottoms of stripper 20 supplied through line 21, by bottoms from fractionator 13, by overhead of fractionator 15 or by the $C_8$ aromatic fraction from solvent extraction stage 18. Each of these feeds will contain the xylenes generated in reformer 11 in association with more or less paraffins and/or aromatics boiling in the xylene range or higher. If the feed is taken from ethylbenzene stripper 20 bottoms, it is supplied directly to a p-xylene separator 22 mixed with a recycle stream presently to be described. In separator 22, p-xylene is separated from the mixture by any of the known techniques. The residue from separator 22 passes by line 23 to reactor 24 containing catalyst consisting essentially of low activity zeolite having a silica/alumina ratio greater than 12 and a constraint index of 1-12, combined with a hydrogenation metal. A stream of normal or slightly branched paraffins is added by line 31 to the charge for reactor 24 which is operated under hydrogen pressure.

Under the high temperature conditions prevailing in reactor 24, that catalyst has capacity (1) to isomerize xylenes thereby restoring equilibrium concentrations in the mixed xylenes of the feed from separator 22 to generate addition p-xylene, (2) to remove alkyl chains of two or more carbon atoms from single ring aromatics, leaving methyl groups to thereby generate BTX, and (3) to crack paraffins to lower boiling compounds which can be removed in the downstream fractionators. The invention therefor contemplates adding to the feed for reactor 24 streams which contain paraffins and/or aromatics of more than eight carbon atoms. Such streams are provided by bottoms of fractionator 13 or overhead of fractionator 15 which may be solvent extracted, if desired, by equipment like solvent extraction stage 18. Similarly, EB tower 20 may be dispensed with. One such variant is illustrated in the drawing by broken line as feed pipe 25 to transfer tower 13 bottoms to the feed for reactor 24.

The effluent of reactor 24 in line 26 contains the three xylenes in proportions approaching the thermodynamic equilibrium value together with conversion products from reaction of ethylbenzene and higher boiling alkyl aromatics as well as a portion of unreacted ethylbenzene and higher. The by-products will include benzene, toluene and xylenes derived by reactions of such compounds of ethylbenzene, methylethylbenzene, dimethylethylbenzene, etc. The reaction mixture is fractionated in column 27 to take compounds of five carbon atoms and less overhead, benzene and toluene as a side stream and bottoms substantially constituted by aromatics of eight or more carbon atoms. That bottoms fraction passes by line 28 to fractionator 29 to remove aromatics of nine or more carbon atoms as bottoms. The overhead fraction of eight carbon atom aromatics is transferred by line 30 as feed to separator 22.

The heavy aromatics in the bottoms of column 29 are not advantageously recycled to the reactor as in some other processes. The lack of transalkylation activity in the catalyst of this invention renders it incapable of generating substantial amounts of xylenes by reaction of, e.g. trimethylbenzene. Column 29 bottoms may be subjected to reaction with toluene in a separate heavy aromatics reactor to produce xylenes and the reaction product added to the loop at line 26 as described in application Ser. No. 945,279, filed Sept. 25, 1978 or may be diverted to motor fuel blending.

The reactor 24 contains a crystalline aluminosilicate (zeolite) catalyst of relatively low acidity. That catalyst promotes a reaction course which is unique at temperatures upwards to 800° F. Ethylbenzene in the charge is selectively cracked to benzene at little or no conversion of xylenes. Two or more carbon atom chains on other aromatics undergo like conversion. The two types of conversion are decoupled such that, for the first time, reaction severity is not a compromise to achieve effective ethyl aromatic conversion at "acceptable" loss of xylene. This characteristic of the process renders unnecessary the preliminary distillation to separate at least some of the ethyl benzene and $C_9+$ aromatics from the feed stream as practiced in prior processes. It has been disclosed in the said Morrison and Tabak applications that the process has capability to convert paraffin hydrocarbons. This makes it possible to dispense with the expensive extraction step conventionally applied to a fraction of catalytically reformed naphthas in the manufacture and recovery of xylenes. In taking advantage of this feature, the feed stream at line 25 will contain the $C_8+$ aromatics of a reformate or the like together with the paraffins of like boiling range, e.g. nonanes, and heavier. The paraffins in the charge are hydrocracked to lighter paraffins which will come off column 27 in much greater quantity than that resulting from conversion of ethylbenzene.

According to the present invention, normal and slightly branched paraffins are added to the reactor charge in order to further improve conservation of xylenes. In many instances, as demonstrated hereafter, a net gain of xylenes is realized for reasons which are not fully understood at the present time. The term "slightly branched" refers to paraffins in which no carbon atom bears substituents in excess of a single methyl group.

Particularly preferred catalysts for reactor 24 are those zeolites having a constraint index within the approximate range of 1 to 12. Zeolites characterized by such constraint indices induce profound transformations of aliphatic hydrocarbons to aromatic hydrocarbons in commercially desirable yields and are generally highly effective in conversion reactions involving aromatic hydrocarbons. These zeolites retain a degree of crystallinity for long periods in spite of the presence of steam at high temperature which induces irreversible collapse of the framework of other zeolites, e.g. of the X and A type. Furthermore, carbonaceous deposits when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination, a silica to alumina mole ratio of at least about 12; and a structure providing constrained access to the crystalline free space.

In one embodiment, the desired low activity is achieved by unusually high silica/alumina ratio, greater than 200, preferably above 500.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Such zeolites, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromotography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methyl pentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
| --- | --- |
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperatures employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with probability, in some instances, of compounding variables extremes.

While the above experimental procedure will enable one to achieve the desired overall conversion of 10 to 60% for most catalyst samples and represents preferred conditions, it may occasionally be necessary to use somewhat more severe conditions for samples of very low activity, such as those having a very high silica to alumina ratio. In those instances, a temperature of up to about 1000° F. and a liquid hourly space velocity of less than one, such as 0.1 or less, can be employed in order to achieve a minimum total conversion of about 10%.

The class of zeolites defined herein is exemplified by ZSM-5, ZSM-11, ZSM-12, ZSM-35, ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-35 is more particularly described in U.S. Pat. No. 4,016,245, the entire contents of which are incorporated herein by reference.

ZSM-38 is more particularly described in U.S. Pat. No. 4,046,859, the entire contents of which are incorporated herein by reference.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicate are ZSM-5, ZSM-11, ZSM-12, ZSM-35, and ZSM-38, with ZSM-5 or its metal containing variant particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired. Therefore, the preferred zeolites of this invention are those having a constraint index as defined above of about 1 to about 12, a silica to alumina ratio of at least about 500 and a dried crystal density of not less than about 1.6 grams per cubic centimeter. The dry density for known structures may be calculated from the number of silicon plus aluminum atoms per 1000 cubic Angstroms, as given, e.g. on page 19 of the article on Zeolite Structure by W. M. Meier. This paper, the entire contents of which are incorporated herein by reference, is included in "Proceedings of the Conference on Molecular Sieves, Longon, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clays, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolines commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with the porous matrix material, such an alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99 percent by weight and more usually in the range of about 5 to about 80 percent by weight of the composite.

The invention utilizes zeolites of the type described, limited however to those forms which are of relatively low acidity. It has been found that, as the acid activity of these zeolites is reduced, the capacity to catalyze disproportionation declines without substantial decline in the capacity to catalyze isomerization of xylenes at temperatures above about 800° F. The invention takes advantage of that unique characteristic to achieve the processing advantage that isomerization is decoupled from ethylbenzene conversion which now proceeds by dealkylation in the presence of the low acidity zeolite. A significant consequence of these catalytic properties is that recycle of toluene and trimethylbenzene to the reactor is generally undesirable. The lack of disproportionation activity means that these methylbenzenes will not be converted in significant amounts to xylenes. Hence recycle of these unreactive species results in undesirable build-up in the loop of diluent materials.

The low acid activity of the catalyst is attainable in any of several ways or a combination of these. A preferred alternative is to form the zeolite at high silica/alumina ratio above 200, preferably above 500. Very high dilution with an inert matrix is also effective. For example, composites of more active form of zeolite ZSM-5 with alumina at a ratio of 5 parts of zeolite with 95 parts of the inert matrix provides a suitable catalyst as described in application Ser. No. 795,046, filed May 9, 1977, now abandoned, the entire contents of which are incorporated herein by reference.

Activity of these zeolites may be reduced to levels suited to practice of the invention by thermal treatment or steam at high temperature as described in application Ser. No. 585,025, filed May 22, 1975, now U.S. Pat. No. 4,015,537, and in Pat. No. 3,965,209, respectively. Zeolites employed in such severe reactions as aromatization of paraffins and olefins lose activity to an extent which makes them suitable for use in the process of this invention. See U.S. Pat. No. 3,960,978 for fuller discussion of this manner of deactivated zeolite. Another method for reducing activity is to provide basic cations such as sodium at a significant proportion of the cationic sites of the zeolite. That technique is described in U.S. Pat. No. 3,899,544.

In many cases, steaming will be the preferred manner of reducing the acid activity of the zeolite catalyst. That catalyst preparation step may be conducted in situ by passing steam at suitable temperature, generally 1000° F. or higher through catalyst in reactor 24 for a period of several hours until the desired reduction in disproportionation activity is achieved.

By whatever means the reduced acid activity is achieved, the activity may be measured in terms of disproportionation activity. A suitable test for the purpose involves contacting xylenes in any convenient mixture or as a single pure isomer over the catalyst at 900° F., 200 psig and liquid hourly space velocity (LHSV) of 5. Suitable catalysts for use in the process of the invention will show a single pass loss of xylenes (by disproportionation) of less than 2 weight percent, preferably less than one percent. Catalysts which have been employed show losses in the neighborhood of 0.5 percent. It is this very low rate if disproportionation at very high levels of ethylbenzene conversion to benzene (about 30%) that provides the advantage of the new chemistry of aromatics processing characteristic of the invention. That lack of disproportionation (and transalkylation generally) activity also dictates withdrawal of compounds boiling above and below eight carbon atom aromatic compounds. For example, toluene and trimethyl benzene are converted to very little, if any, extent and become diluents which occupy reactor space to no advantage. Small amounts of such diluents can be tolerated, such as those present by reason of "sloppy" fractionation, but withdrawal to at least a major extent is important to efficient operation.

Little difference in process chemistry is found with ZSM-5 catalyst of low activity achieved by techniques other than steaming, though tests of these showed higher aging rates as measured by the temperature increase required to maintain constant ethylbenzene conversion. A catalyst of ZSM-5 having a silica/alumina ratio of 1600 aged at a rate of about 2° F. per day. A bulk diluted catalyst of 2% ZSM-5 with 98% alumina matrix aged at a rate of about 5° F. per day.

In many operations to prepare charge for p-xylene manufacture, the $C_8$ reformate cut is extracted with Sulfolane (dioxytetrahydrothiophene) to separate paraffins. The aromatic extract can contain traces of the selective solvent which can be detrimental to some catalysts. After 22 days on stream, steamed ZSM-5 was exposed to charge containing 290 ppm Sulfolane (80 ppm Sulfur) for 22 hours with no measurable aging effect. This was followed by 725 ppm Sulfolane (200 ppm Sulfur) for 21 hours, which resulted in about 13° F. of aging. By way of contrast, addition of 360 ppm Sulfolane (100 ppm Sulfur) in the process of U.S. Pat. No. 4,101,596 resulted in 50°–100° F. of aging after 24 hours.

THE PARAFFIN ADDITIVE

It will be recognized from the foregoing discussion that certain charge fractions contemplated by the invention will contain paraffin hydrocarbons as constitutents of a reformate which has not been extracted to separate those compounds. The paraffins so present in reformate will be constituted by mixtures of isomers approximating the thermodynamic equilibrium because the reforming catalyst of platinum on silica-alumina is a powerful isomerization catalyst. For purposes of this invention, the isomerizer feed will contain 5 to 25 weight percent, preferably about 10%, of paraffins which are normal or which have no carbon atom with substituents in excess of a single methyl group. Those paraffins preferably are in the range of three to twelve carbon atoms, with n-nonane being particularly preferred. Paraffins of more than six carbon atoms give best results.

Such concentrations of this limited class of paraffins are not generally found in reformates and it is necessary, in practice of the invention to add a stream containing the paraffin additive. The additive may be introduced at any point in the system which will result in the desired concentration in the reactor feed. It is preferred to add the paraffins directly to the reactor feed in order that they shall not increase the load on fractionators, the separator and other equipment upstream of the reactor. The amount of paraffin, added to the reactor feed can be adjusted to supplement those present in the reformate or may be scheduled as a constant quantity, such as 10 weight percent of n-nonane based on reactor feed.

The process of this invention is shown below to result in a shift from net xylene loss in the overall system to net xylene gain with addition of n-nonane. Any reduction of the xylene loss per pass is a greater gain than would appear from the actual values observed. About 75% of the xylenes are recycled in the process and the overall loss of xylene is therefore a significant multiple of the single pass loss, approximating 6–10% in many commercial processes.

EXAMPLE 1

A co-crystallized platinium ZSM-5 was prepared according to the technique described in application Ser. No. 912,681, filed June 5, 1978 to contain 0.2 weight percent platinium with ZSM-5 of 1600/1 silica/alumina ratio. This catalyst was tested with low paraffin and high paraffin charge stock under conditions shown in Table 1 which also lists charge stock composition and results obtained. Conversion of ethylbenzene is at a good level and the approach of xylene concentrations to the thermodynamic equilibrium ("XYLENES EQUIL. APPR.") is very good. Very significant is the shift from xylene loss without paraffin to xylene gain when n-nonane was added. Also interesting is the ratio of moles of benzene formed per mol of ethylbenzene converted ("Bz/ΔEB").

TABLE 1

| Conditions | | | | | | |
|---|---|---|---|---|---|---|
| Temp. °F. | 900 | 860 | 890 | 890 | 912 | 911 |
| Pressure, PSIG | 200 | 200 | 200 | 200 | 200 | 200 |
| WHSV | 30 | 30 | 20 | 20 | 20 | 10 |

TABLE 1-continued

| | | | | | | |
|---|---|---|---|---|---|---|
| $H_2/HC$ | 5 | 5 | 5 | 5 | 5 | 5 |
| Time On Stream, Hr. | 4 | 9 | 12 | 20 | 22 | 28 |
| EB Conversion, WT PCT | 31.8 | 17.2 | 35.1 | 29.5 | 34.3 | 51.0 |
| N-$C_9$ Conversion, WT PCT | | | | 24.0 | 28.3 | 43.5 |
| Bz/ΔEB | 0.84 | 1.04 | 0.88 | 0.92 | 0.97 | 0.96 |
| Xylene Gain | −0.80 | −0.42 | −1.27 | 1.91 | 0.75 | 1.27 |
| Xylenes Equil. Appr. % | | | | | | |
| P- | 98 | 89 | 98 | 100 | 101 | 101 |
| O- | 62 | 56 | 67 | 77 | 80 | 90 |
| Feed Blend, WT PCT | | | | | | |
| EB | 19.9 | 19.9 | 19.9 | 28.8 | 28.8 | 28.8 |
| P-Xylene | 9.2 | 9.2 | 9.2 | 7.4 | 7.4 | 7.4 |
| M-Xylene | 60.4 | 60.4 | 60.4 | 48.5 | 48.5 | 48.5 |
| O-Xylene | 10.5 | 10.5 | 10.5 | 3.2 | 3.2 | 3.2 |
| N-$C_9$ | 0 | 0 | 0 | 11.9 | 11.9 | 11.9 |

EXAMPLE 2

Table 2 is a similar report of runs with a catalyst of 0.2 weight percent platinum impregnated on the sodium form of ZSM-5 at 70/1 silica/alumina ratio.

TABLE 2

| Conditions | | | | | | |
|---|---|---|---|---|---|---|
| Temp. °F. | 870 | 919 | 847 | 870 | 891 | 875 |
| Pressure, PSIG | 200 | 200 | 200 | 200 | 200 | 200 |
| WHSV | 30 | 30 | 45 | 30 | 30 | 20 |
| $H_2/HC$ | 5 | 5 | 3.5 | 5 | 5 | 5 |
| Time On Stream, Hr. | 5 | 8 | 12 | 17 | 21 | 24 |
| EB Conversion, WT PCT | 29.4 | 45.1 | 16.8 | 26.1 | 44.7 | 38.9 |
| N—$C_g$ Conversion, WT PCT | 100 | 100 | 89.5 | | | |
| Bz/ΔEB | 0.96 | 0.99 | 0.94 | 0.94 | 0.92 | 0.88 |
| Xylene Gain | 0.74 | −0.20 | 0.23 | −1.40 | −3.11 | −3.66 |
| Xylene Equil. Appr. | | | | | | |
| P- | 100 | 101 | 100 | 100 | 101 | 99 |
| O- | 84 | 87 | 74 | 88 | 82 | 83 |
| Feed Blend, WT PCT | | | | | | |
| EB | 28.4 | 28.4 | 28.4 | 10.3 | 10.3 | 10.3 |
| P-Xylene | 7.0 | 7.0 | 7.0 | 10.2 | 10.2 | 10.2 |
| M-Xylene | 47.3 | 47.3 | 47.3 | 67.6 | 67.6 | 67.6 |
| O-Xylene | 4.8 | 4.8 | 4.8 | 11.7 | 11.7 | 11.7 |
| N—$C_g$ | 12.2 | 12.2 | 12.2 | 0 | 0 | 0 |

EXAMPLE 3

The catalyst used in further comparative runs was prepared as follow: a mixture of ZSM-5 and alumina (50/50) was mulled with an aqueous solution of $Pt(NH_3)_4Cl_2$ containing sufficient Pt to result in 0.1% Pt on final catalyst (dry basis) and sufficient water for extrusion. The mixture was formed into 1/16 in diameter pellets by extrusion. The catalyst pellets were calcined in nitrogen at 1000° F. (3 hrs.), then exchanged with ammonium nitrate to reduce the sodium content to 0.001%. The catalyst was dried, calcined at 1000° F. in air and subsequently steamed for 3 hrs. at 1000° F. with 100% steam at 0 psig. The pertinent data are given in Table 3. Note that the feed for these experiments contains 25.3% isooctane (I-$C_8$, 2, 2, 4-trimethyl-pentane) as well as n-nonane. Cracking of n-nonane is considerably greater than for isooctane, since the branched paraffin cannot be converted within the zeolite pores.

TABLE 3

| Conditions | | | | |
|---|---|---|---|---|
| Temp. °F. | 869 | 871 | 873 | 874 |
| Pressure, PISG | 200 | 200 | 200 | 200 |
| WHSV | 7.0 | 13.4 | 10.0 | 10.0 |
| $H_2/HC$ | 5.7 | 6.1 | 2.3 | 2.3 |
| Time on Stream, Hr. | 24.0 | 46.1 | 24.0 | 48.0 |
| EB Conversion, WT PCT | 60.6 | 37.7 | 62.6 | 61.9 |
| N-$C_9$ Conversion, WT PCT | 86.0 | 40.7 | 73.5 | 68.9 |
| Iso-$C_8$ Conversion, WT PCT | 34.6 | 19.2 | 16.8 | 14.8 |
| Bz/ΔEB | 0.72 | 0.80 | 0.82 | 0.82 |
| Xylene Gain | −2.2 | −0.6 | 1.2 | 0.4 |
| Xylenes Equil. Appr. % | | | | |
| P- | 113 | 109 | 115 | 115 |
| O- | 94 | 89 | 94 | 94 |
| Feed Blend, WT PCT | | | | |
| EB | 14.3 | 14.3 | 12.2 | 12.2 |
| P-Xylene | 12.0 | 12.0 | 10.6 | 10.6 |
| M-Xylene | 62.7 | 62.7 | 55.7 | 55.7 |
| O-Xylene | 5.8 | 5.8 | 5.1 | 5.1 |
| N-$C_9$ | 2.8 | 2.8 | 13.9 | 13.9 |
| Iso-$C_8$ | 2.9 | 2.9 | 2.5 | 2.5 |

It is clear that over the same catalyst, high paraffin containing feeds resulted in a xylene gain while low paraffin containing feeds resulted in a xylene loss. As an example, in Table 1, at around 30% EB conversion, the Pt cocrystallized high silica ZSM-5 had a xylene gain of 1.9% with 12% paraffin in the feed compared to a xylene loss of 0.8% with no paraffins in the feed. As another example, in Table 2, at around 30% EB conversion, the NaZSM-5 catalyst showed a 0.7% xylene gain compared to a 1.4% xylene loss when high paraffin feed (i.e., 12% N-$C_9$) was switched to non-paraffin containing feed. As a further example, in Table 3, at 60% EB conversion, the Pt impregnated high silica ZSM-5 showed a 2.2% xylene loss compared to a 1.2% xylene gain when low paraffin feed was switched to high paraffin feed containing 13.9% N-$C_9$ and 2.5% iso-$C_8$.

In each case in which xylene gains are observed, the paraffin present is n-nonane ($C_9$). The product distributions show no evidence of aromatization of the $C_9$ paraffins to aromatics, particularly $C_8$ aromatics. Further the reaction conditions and catalyst metal function (Pt) make it unlikely that cracked fragments (olefins) are being aromatized by the ZSM-5 function: in fact, only negligible amounts of light olefins are observed, since they are rapidly hydrogenated. It is probable, then, that the presence of paraffins is in some way promoting isomerization of ethylbenzene to xylenes.

What we claim is:

1. A new use of known apparatus for simultaneously isomerizing xylenes and converting ethylbenzene to products readily separable by distillation from the mixture of $C_8$ aromatics by contacting a mixture of $C_8$ aromatics with a catalyst at conversion conditions of elevated temperature and under hydrogen pressure in a loop comprising an isomerization reactor for the contact aforesaid, distillation means for separating $C_8$ aromatics from lower boiling and higher boiling hydrocarbons, means to transfer hydrocarbon effluent of said isomerization reactor to said distillation means, mixing means for mixing fresh feed $C_8$ aromatics containing xylenes and ethylbenzene with $C_8$ aromatics separated by said distillation means, a xylene separator for recovery of para xylene, means for transfer of mixed $C_8$ aromatics from said mixing means to said xylene separator, and means to transfer $C_8$ aromatics lean in para xylene from said xylene separator to said isomerization reactor, which new use comprises contacting, in the isomerization reactor of said known apparatus, a vapor phase mixture of said $C_8$ aromatics lean in para xylene together with 5 to 25 weight percent based on total charge to said reactor of paraffin hydrocarbon having 3 to 12 carbon atoms and having no branching in excess of one methyl group on any one carbon atom and fresh charge material containing alkyl benzenes of more than eight carbon atoms with a zeolite catalyst at a temperature of about 800°-1000° F., a pressure of less than 100 pounds per square inch and a weight hourly space velocity between 1 and about 200; said zeolite catalyst having a constraint index of 1 to 12, a silica to alumina ratio greater than 12 and a reduced acidity such that less than 2 weight percent of xylene is converted to other compounds when contacted with said catalyst at 900° F., 200 psig and LHSV of 5.

2. The new use defined by claim 1, wherein said zeolite is in the acid form.

3. The new use defined by claim 1, wherein said silica to alumina ratio is greater than 200.

4. The new use defined by claim 1, wherein said silica to alumina ratio is greater than 500.

5. The new use defined by claim 1, wherein said paraffin hydrocarbon is n-nonane.

6. The new use defined by claim 1, wherein said paraffin hydrocarbon is about 10 weight percent of said total charge.

7. In a process for isomerizing the xylene content of a charge mixture of eight carbon atoms aromatic hydrocarbon compounds which mixture contains xylene, and ethylbenzene by contact at conversion conditions under hydrogen pressure with a catalyst comprising a zeolite having a silica/alumina ratio greater than 12 and a constraint index of 1 to 12, the improvement resulting in conversion of ethylbenzene to benzene and conversion of higher alkyl benzenes to benzene, toluene and xylene which comprises including in the charge mixture 5-25 weight percent based on total charges of paraffin hydrocarbons having 3-12 carbon atoms and having no branching in excess of one methyl group on any carbon atom, maintaining the conversion pressure at more than 100 pounds per square inch and the conversion temperature of about 800° F. to 1000° F. and using such catalyst comprising a zeolite of reduced acid acidity such that less than 2 weight percent of xylene is converted to compounds other than xylene when contacted with said catalyst at 900° F., 200 psig and LHSV of 5.

8. A process according to claim 7, wherein said zeolite is in the acid form.

9. A process according to claim 7, wherein said zeolite is ZSM-5.

10. A process according to claim 7, wherein said zeolite comprises alkali metal cations.

11. A process according to claim 7, wherein the concentration of said paraffin hydrocarbon is about 10%.

12. A process according to claim 7, wherein said zeolite is ZSM-5 which has been steamed.

13. A process according to claim 7, resulting in conversion of ethylbenzene to benzene at substantially no loss of xylene in the product as compared to the charge.

14. A process according to claim 7, wherein the paraffin hydrocarbon is n-nonane.

15. A process according to claim 7, wherein the catalyst also contains a Group VIII metal.

16. A process according to claim 7, wherein said silica/alumina ratio is greater than 200.

17. A process according to claim 7, wherein said silica/alumina ratio is greater than 500.

18. A process for the manufacture of aromatic hydrocarbons which comprises subjecting a hydrocarbon naphtha to catalytic reforming under conditions to convert naphthenes to aromatic hydrocarbons in a reformate reaction product, distilling said reformate to separate compounds of less than eight carbons from a heavy reformate, mixing said heavy reformate with a recycle stream hereafter defined, contacting the resultant mixture together with hydrogen and 5-25 weight percent based on said mixture of paraffin hydrocarbon having 3-12 carbon atoms and no branching in excess of one methyl group on any carbon atom at pressure above about 100 pounds per square inch and a temperature of about 800°-1000° F. with a zeolite catalyst having a constraint index of 1 to 12, a silica/alumina ratio above about 12 and reduced acidity such that less than 2 weight percent of xylene is converted to compounds other than xylene when contacted with said catalyst at 900° F., 200 psig and LHSV of 5, whereby to isomerize xylene content of said mixture and to convert ethylbenzene and alkylbenzenes of more than eight carbon atoms to benzene, toluene and xylene, distilling the product of said contacting to separate compounds of less than eight carbon atoms and compounds of more than eight carbon atoms from a $C_8$ fraction, recovering at least one xylene isomer from said $C_8$ fraction to provide a stream lean in said recovered isomer and mixing said lean stream with said heavy reformate as the recycle stream aforesaid.

19. A process according to claim 18 wherein said zeolite is ZSM-5.

20. A process according to claim 18 wherein said zeolite is in the acid form.

21. A process according to claim 18 wherein the amount of said paraffin hydrocarbon is about 10%.

22. A process according to claim 18 wherein said heavy reformate is treated with a solvent to separate paraffins therefrom.

23. A process according to claim 18 wherein said paraffin hydrocarbon is n-nonane.

24. A process according to claim 18 wherein said silica/alumina ratio is greater than 200.

25. A process according to claim 18 wherein said silica/alumina ratio is greater than 500.

26. In a process for manufacture of a desired xylene isomer which comprises separating the desired xylene isomer from a mixture containing the three xylene isomers, isomerizing the resultant mixture lean in at least one isomer to generate additional amounts of said desired isomer, separating compounds of boiling point higher and lower than xylenes from the isomerization product to provide a recycle stream, mixing said recycle stream with additional aromatic compounds of eight carbon atoms including the three xylene isomers and supplying the resultant mixture to the step aforesaid of separating a desired isomer, the improvement which comprises isomerizing the said mixture lean in a desired isomer in admixture with hydrogen and 5-25 weight percent of paraffin hydrocarbon of 3-12 carbon atoms having no branching in excess of one methyl group on any carbon atom at a temperature of about 800°-1000° F., a pressure above about 100 pounds per square inch and a weight hourly space velocity between 1 and about 200 by contact with a zeolite catalyst having a constraint index of 1 to 12, a silica to alumina ratio greater than 12 and a reduced acidity such that less than 2 weight percent of xylene is converted to other compounds when contacted with said catalyst at 900° F., 200 psig and LHSV of 5.

27. The process of claim 26 wherein said zeolite is in the acid form.

28. The process of claim 26 wherein said silica to alumina ratio is greater than 200.

29. The process of claim 26 wherein said silica to alumina ratio is greater than 500.

30. The process of claim 26 wherein said zeolite has been steamed to achieve said reduced activity.

31. The process of claim 26 wherein said zeolite is composited with an inert matrix material in an amount such that the inert matrix constitutes at least 90% of the composite.

32. The process of claim 26 wherein said zeolite contains alkali metal cations.

33. The process of claim 26 wherein said paraffin hydrocarbon is n-nonane.

34. The new use defined by claim 1 wherein said paraffin hydrocarbon has more than six carbon atoms.

35. The new use defined by claim 1 wherein said catalyst also contains a Group VIII metal.

36. The new use defined by claim 35 wherein said metal is platinum.

37. A process according to claim 7 wherein said paraffin hydrocarbon has more than six carbon atoms.

38. A process according to claim 15 wherein said metal is platinum.

39. A process according to claim 18 wherein said paraffin hydrocarbon has more than six carbon atoms.

40. A process according to claim 18 wherein said catalyst also contains a Group VIII metal.

41. A process according to claim 40 wherein said metal is platinum.

42. A process according to claim 26 wherein said paraffin hydrocarbon has more than six carbon atoms.

43. A process according to claim 26 wherein said catalyst also contains a Group VIII metal.

44. A process according to claim 43 wherein said metal is platinum.

* * * * *